(12) United States Patent
Furuya

(10) Patent No.: US 11,116,896 B2
(45) Date of Patent: Sep. 14, 2021

(54) INFUSION PUMP INSPECTION MACHINE

(71) Applicant: TRI-TECH CORPORATION, Fuji (JP)

(72) Inventor: Akihiko Furuya, Fuji (JP)

(73) Assignee: TRI-TECH CORPORATION, Fuji (JP)

( * ) Notice: Subject to any disclaimer, the term of this patent is extended or adjusted under 35 U.S.C. 154(b) by 207 days.

(21) Appl. No.: 16/494,112

(22) PCT Filed: Jan. 30, 2018

(86) PCT No.: PCT/JP2018/002888
§ 371 (c)(1),
(2) Date: Sep. 13, 2019

(87) PCT Pub. No.: WO2018/211746
PCT Pub. Date: Nov. 22, 2018

(65) Prior Publication Data
US 2020/0360605 A1  Nov. 19, 2020

(30) Foreign Application Priority Data

May 18, 2017  (JP) .............................. JP2017-099229

(51) Int. Cl.
*A61M 5/168*  (2006.01)
*A61M 5/142*  (2006.01)
*A61J 1/10*  (2006.01)

(52) U.S. Cl.
CPC ........ *A61M 5/16831* (2013.01); *A61M 5/142* (2013.01); *A61M 5/1689* (2013.01);
(Continued)

(58) Field of Classification Search
CPC ................ A61M 5/1456; A61M 5/142; A61M 5/14546; A61M 5/14566; A61M 5/1452;
(Continued)

(56) References Cited

FOREIGN PATENT DOCUMENTS

| JP | H08-276008 A | 10/1996 |
|----|--------------|---------|
| WO | 99/058178 A1 | 11/1999 |

OTHER PUBLICATIONS

Apr. 24, 2018 International Search Report issued in International Patent Application No. PCT/JP2018/002888.
(Continued)

*Primary Examiner* — Manuel A Mendez
(74) *Attorney, Agent, or Firm* — Oliff PLC

(57) ABSTRACT

An inspection machine checks and inspects whether an infusion pump is accurately operated and does not require maintenance in a closed system without drainage. This inspection machine includes a syringe and a plunger and moves the plunger backward when an infusion flows into the syringe through a communication hole by the driving of an infusion pump to measure a flow rate by the backward movement amount. An outer peripheral surface of the plunger has an annular recess and a seal ring is fitted thereto. The seal ring is expanded by receiving a liquid pressure of the infusion to be sealed and the plunger is coaxially centered on the syringe. The flow rate of the infusion is accurately reflected to the plunger movement amount. Further, since the infusion is stored in the syringe and does not drip, drainage equipment is not required and an inspection operation can be performed anywhere.

7 Claims, 8 Drawing Sheets

(52) U.S. Cl.
CPC ....... *A61J 1/10* (2013.01); *A61M 2005/16863* (2013.01); *A61M 2205/18* (2013.01); *A61M 2205/3306* (2013.01); *A61M 2205/3584* (2013.01); *A61M 2205/502* (2013.01); *A61M 2205/52* (2013.01); *A61M 2205/8206* (2013.01); *A61M 2209/02* (2013.01)

(58) Field of Classification Search
CPC .............. A61M 5/14216; A61M 5/145; A61M 5/14228; A61M 5/3145; A61M 5/007; A61M 5/14248; A61M 5/14526; A61M 5/16831
See application file for complete search history.

(56) References Cited

OTHER PUBLICATIONS

Apr. 24, 2018 Written Opinion issued in International Patent Application No. PCT/JP2018/002888.

INFUSION PUMP INSPECTION MACHINE

TECHNICAL FIELD

The present invention relates to an infusion pump inspection machine.

BACKGROUND ART

As a pump which delivers an infusion, a syringe pump and an infusion pump are known. Since the syringe pump is highly accurate but a total dose is limited, only the infusion pump is used when a total dose is large.

In the infusion pump, as described in Patent Document 1, a dripping number control type which detects a drop of an infusion inside a drip chamber by a drip sensor and controls a flow rate on the basis of a detection result, and a flow rate control type which uses a dedicated tube and controls a flow rate by the drawing number of times of the tube are known. Although the accuracy of both types is lower than that of the syringe pump, it is required to secure the flow rate accuracy at a certain level and to accurately determine an occlusion state in order to perform the infusion safely.

Conventionally, in the inspection of the operation of this infusion pump, water is used instead of the infusion and is stored in a measuring cylinder or container and the flow rate is calculated from a total delivery volume and a total delivery time. Accordingly, the progress could not minutely be recognized on the way.

In recent years, an inspection machine which enables a mechanical inspection is also proposed. However, since a drainage structure is used, a working operation needs to be performed on the side of a sink or a bucket needs to be prepared in advance. In this way, a location is limited or a troublesome work is necessary. Further, a thin wall and small diameter glass pipe is used in order to improve the detection accuracy. When cheap tap water is used, the pipe is easily blocked since the tap water contains various impurities. Accordingly, the pipe needs to be frequently maintained.

CITATION LIST

Patent Document

Japanese Laid Open Patent Document 1: JP-A-hei08-229119

SUMMARY OF THE INVENTION

Technical Problem

The invention has been made in view of the above-described circumstances and an object of the invention is to provide a novel and useful infusion pump inspection machine capable of automatically checking and inspecting whether an infusion pump is accurately operated and not requiring troublesome maintenance in a closed system without drainage.

Solution to Problem

The invention has been made to solve the above-described problems and a first aspect of the invention is an infusion pump inspection machine including: a syringe which has a tube connection communication hole provided in a front end side in an axial direction; and a plunger which is inserted into the syringe by forming a gap so that the plunger is movable forward and backward in the axial direction, in which an operation of an infusion pump is checked and inspected by a liquid flowing into the syringe through the communication hole with the driving of the infusion pump and moving the plunger backward, in which an outer peripheral surface of the plunger is provided with an annular recess, in which a seal ring is fitted to the annular recess, and in which a sealing mechanism which receives a liquid pressure of a liquid flowing into the syringe and filled into the gap so as to expand the seal ring and to increase a contact area with an inner peripheral surface of the syringe and a centering mechanism which coaxially centers the plunger to the syringe are realized.

A second aspect of the invention is the infusion pump inspection machine according to the first aspect, in which the seal ring is a V-shaped seal ring which is fitted so that a V-shaped sharp inner bottom portion faces a base end side of the plunger in the axial direction, and in which the sealing mechanism receives a liquid pressure to expand the V-shape of the seal ring and to increase a contact area with the inner peripheral surface of the syringe.

A third aspect of the invention is the infusion pump inspection machine according to the first or second aspect, in which the plunger is formed to have the same diameter on the front end side in relation to a fitting surface of the seal ring.

A fourth aspect of the invention is the infusion pump inspection machine according to any one of the first to third aspects, in which a locking mechanism for locking a relative movement of the plunger with respect to the syringe and releasing the locking is provided.

A fifth aspect of the invention is the infusion pump inspection machine according to any one of the first to fourth aspects, in which as the measurement unit, a measurement shaft which is provided coaxially with the plunger and moves in synchronization with a backward movement of the plunger, an optical detector which detects a light amount which changes by the movement of the measurement shaft, and a distortion detector which detects distortion generated by the pressing of the measurement shaft are provided, and in which a delivery flow rate is calculated on the basis of a detection result of the optical detector and an occlusion pressure is calculated on the basis of a detection result of the distortion detector.

A sixth aspect of the invention is the infusion pump inspection machine according to any one of the first to fifth aspects, wherein as a pseudo drip signal generator, a pseudo dripper which generates a pseudo drop and an attachment guide portion which attaches a drip sensor of the infusion pump to a position for detecting the pseudo drop are provided.

A seventh aspect of the invention is the infusion pump inspection machine according to any one of the first to sixth aspects, further including: an accommodation portion for a soft bag filled with an infusion.

Advantageous Effects of the Invention

When an infusion pump inspection machine of the invention is used, it is possible to check and inspect whether an infusion pump accurately delivers a liquid at a set flow rate and an alarm is generated at a set occlusion pressure. Further, since an IV set line can be formed as a closed system, drainage is not required. Furthermore, since an especially thin wall and small diameter glass pipe is not used, troublesome maintenance is not required.

MODE FOR CARRYING OUT THE INVENTION

An infusion pump inspection machine 1 according to a first embodiment of the invention will be described with reference to the drawings.

Figure 1:
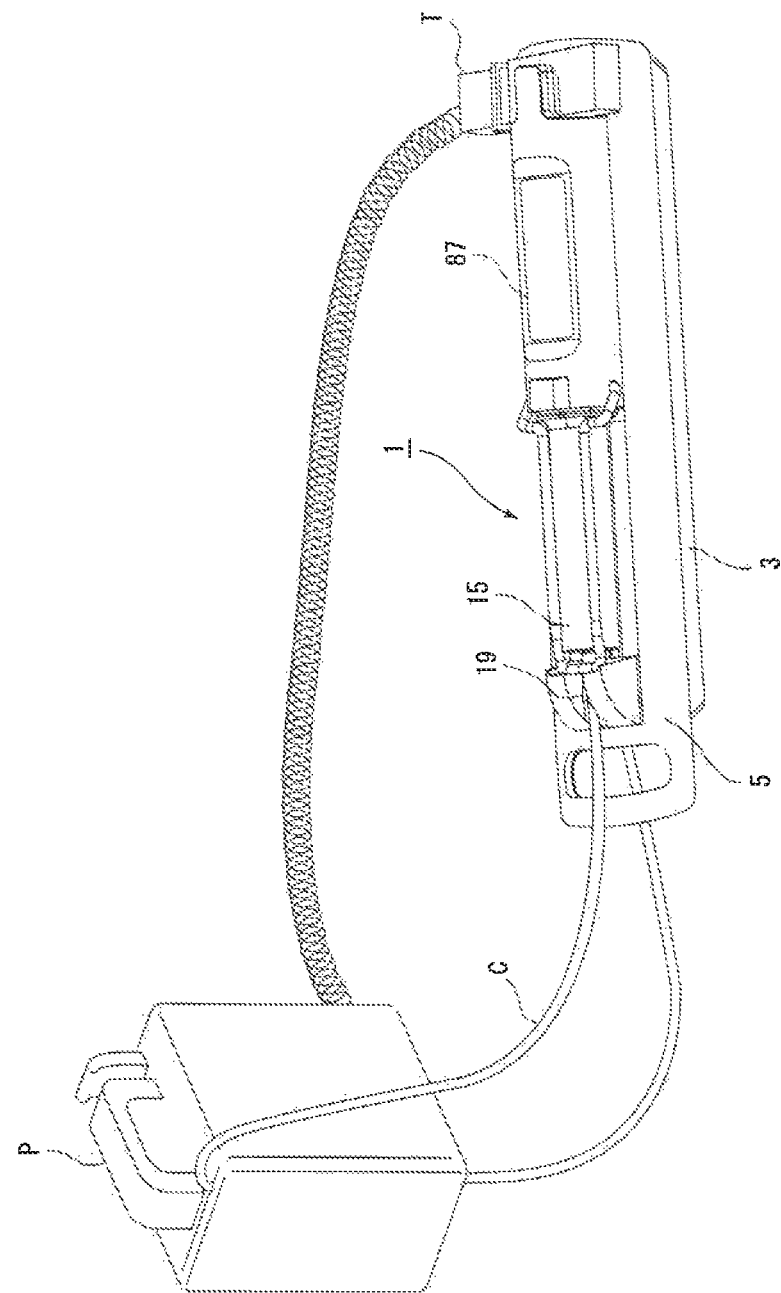
FIG. 1 is an explanatory diagram illustrating a state in which an infusion pump inspection machine according to a first embodiment of the invention is set in an infusion pump.
Figure 6:
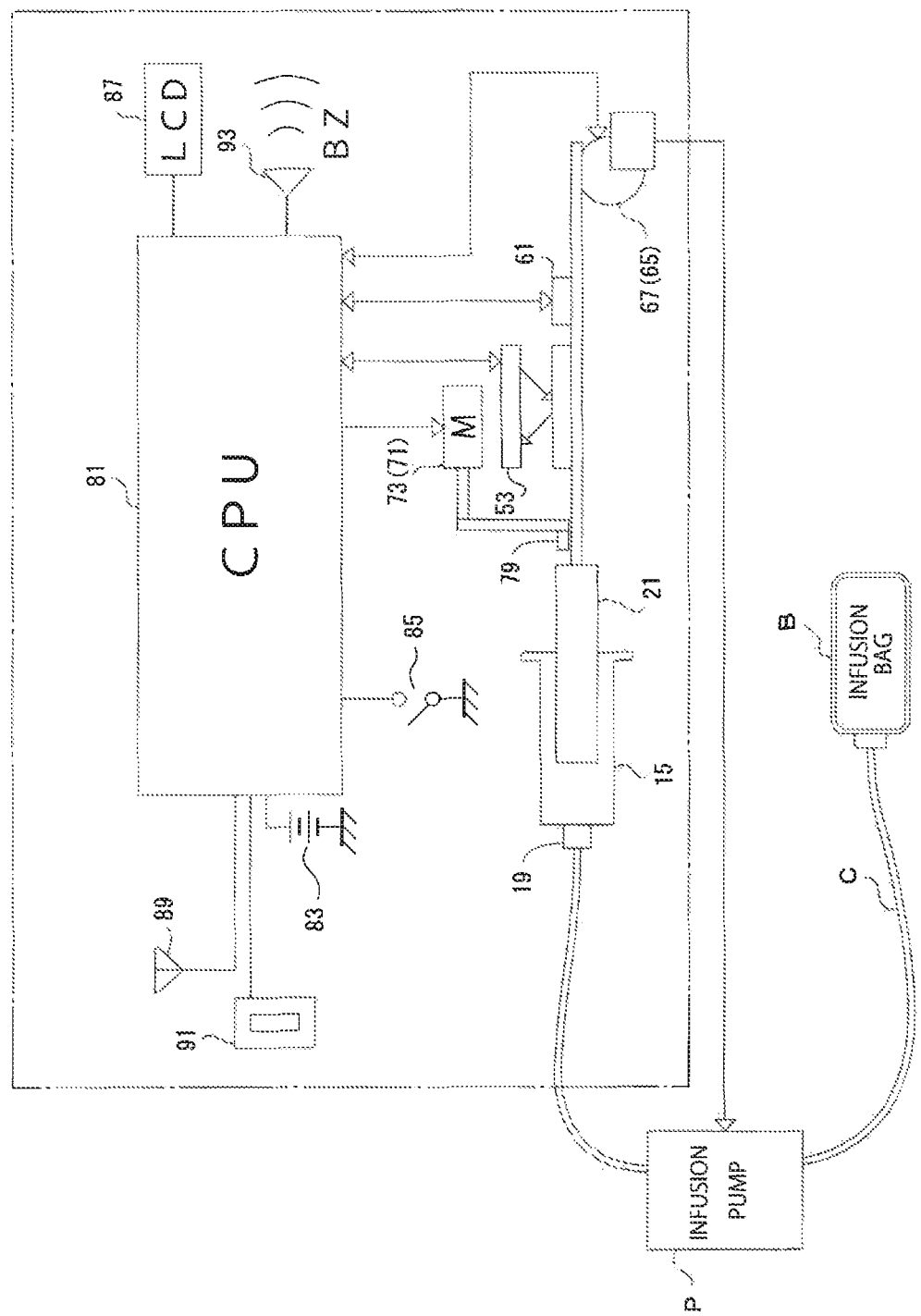
FIG. 6 is an electric configuration diagram of the inspection machine of FIG. 1.

FIG. 1 illustrates a setting state of an inspection machine 1. As illustrated in this drawing, one end side of a tube C attached to an infusion pump P is connected to the inspection machine 1 and the other end side thereof is connected to an infusion bag (a soft bag) B (FIG. 6). The infusion bag B is accommodated in a casing 3 of the inspection machine 1 and the other end side of the tube C is pulled out from a pull-out opening of the casing 3. The casing 3 is attachable to and detachable from a casing body 5. Further, a drip sensor T of the infusion pump P is attached thereto.

Figure 2:
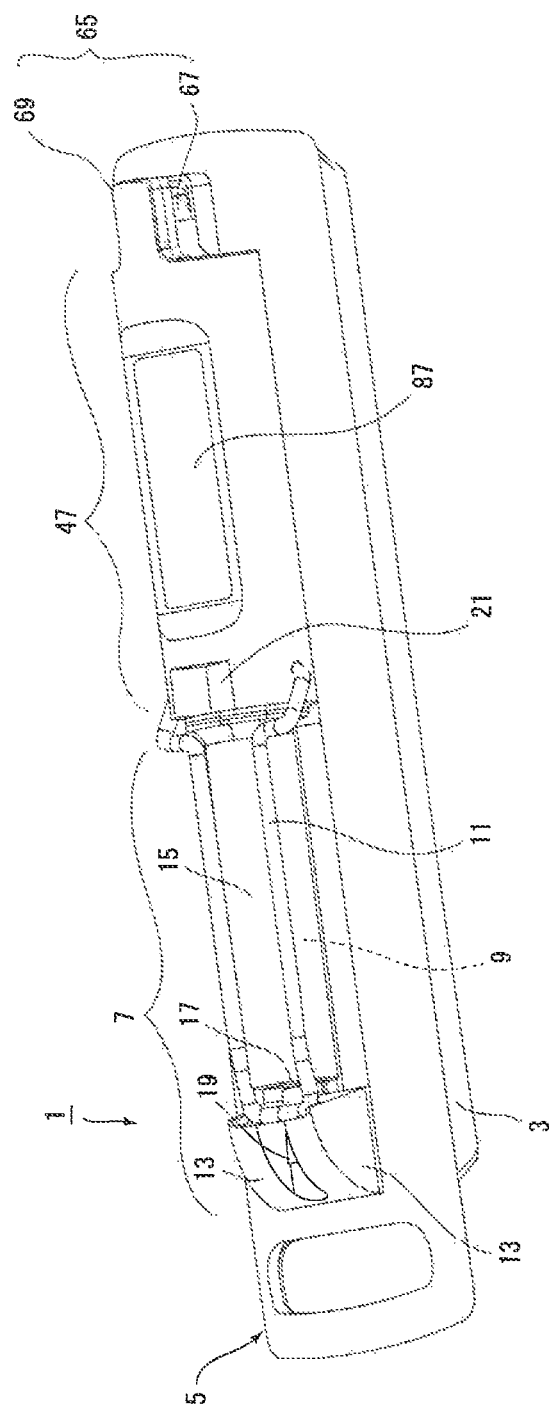
FIG. 2 is a perspective view of the inspection machine of FIG. 1.

In the inspection machine 1, as illustrated in an enlarged view of FIG. 2, the casing body 5 has a rectangular parallelepiped shape and has the casing 3 attached to the lower side thereof in an attachable and detachable manner.

One side of the casing body 5 in the longitudinal direction (the left side of FIG. 2) is formed as a syringe setting portion 7. An upper surface of the syringe setting portion 7 is provided with a bed recess 9 which serves as a syringe bed and is elongated in the longitudinal direction.

A U-shaped guard pipe 11 is rotatably attached to the upper side of the bed recess 9 so as to straddle in the longitudinal direction. The right side of the guard pipe 11 serves as a fulcrum of a base end. When the guide pipe is tilted down, the front end portion of the guard pipe 11 comes to the left end side of the syringe setting portion 7, but a pair of locking recesses 13 and 13 formed by protruding the casing body 5 is provided at that position. Accordingly, when the guard pipe 11 is tilted down, the connection portion is fitted and locked to each of the locking recesses 13 and 13.

Figure 3:
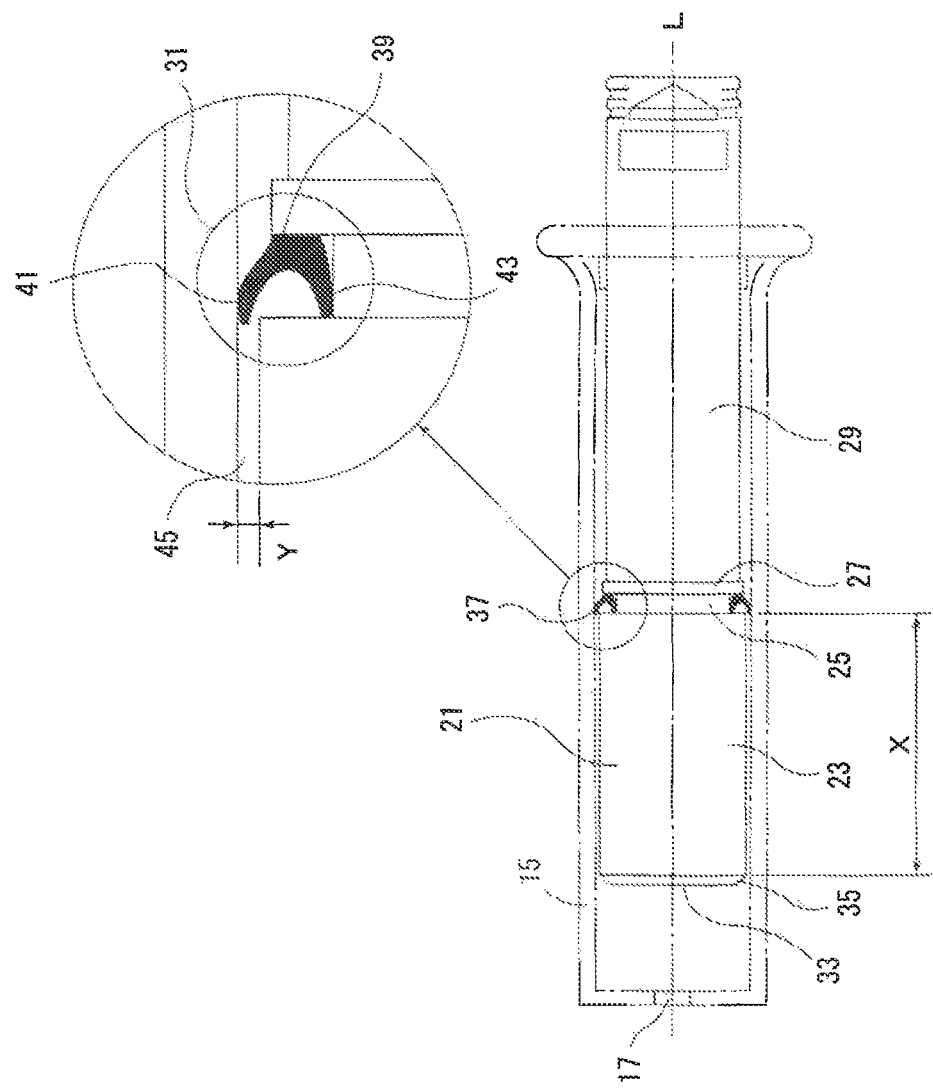
FIG. 3 is a diagram of a relationship between a syringe and a plunger of the inspection machine of FIG. 2.

As illustrated in FIG. 3, a syringe (an outer cylinder) 15 is formed in a straight shape with the same diameter and a narrow circular communication hole 17 is formed at the center of one end side in the axial direction. A tube connection portion 19 (FIG. 1) for the inflow of a liquid is attached to the communication hole 17.

Then, the largely opened other end side serves as an insertion opening of a plunger 21 and the plunger 21 is inserted thereinto so as to be movable forward and backward. In the setting case, the plunger 21 is in an insertion state and the syringe 15 is placed on the bed recess 9 while the tube connection portion 19 is inserted between the pair of locking recesses 13 and 13. Then, when the guard pipe 11 is tilted down to be locked, the guard pipe 11 presses the syringe 15 from above so that the syringe 15 is stably set in the casing body 5.

An insertion relationship between the syringe 15 and the plunger 21 will be described in detail with reference to FIG. 4.

The syringe 15 is molded by glass having a small temperature variation. The plunger 21 is formed of metal into a straight cylindrical shape and both end portions in the axial direction are blocked. A step is provided on the outer peripheral surface of the plunger 21 in the perpendicular direction so that the diameter of the plunger changes and the plunger is divided into a front portion 23, a relay portion 25, a relay portion 27, and a rear portion 29 from a front end side facing the communication hole 17 of the syringe 15 toward a base end side. The relay portions 25 and 27 are remarkably shorter and smaller than the front portion 23 and the rear portion 29 and the diameter decreases in order of the front portion 23, the relay portion 27, the rear portion 29, and the relay portion 25.

An annular recess 31 is formed between the front portion 23 and the relay portion 27.

Further, a front end surface 33 of the front portion 23 is formed as a surface which is perpendicular to the axial direction and a corner portion 35 is chamfered.

A rubber seal ring 37 is fitted to the annular recess 31 of the plunger 21. The seal ring 37 has a V-shape in cross-section and an outer bottom surface 39 of a bottom portion is formed as a plane. The outer bottom surface 39 comes into contact with the step surface of the relay portion 27. Thus, in a tapered outer wall portion 41 and an inner wall portion 43, the inner wall portion 43 elastically contacts the outer peripheral surface of the relay portion 25.

When the plunger 21 is coaxially inserted into the syringe 15, a constant gap 45 is formed between the outer peripheral surface of the front portion 23 of the plunger 21 and the inner peripheral surface of the syringe 15. Further, the front portion 23 has an axial length to a certain degree. Then, the outer wall portion 41 of the seal ring 37 elastically contacts the inner peripheral surface of the syringe 15.

Figure 4:
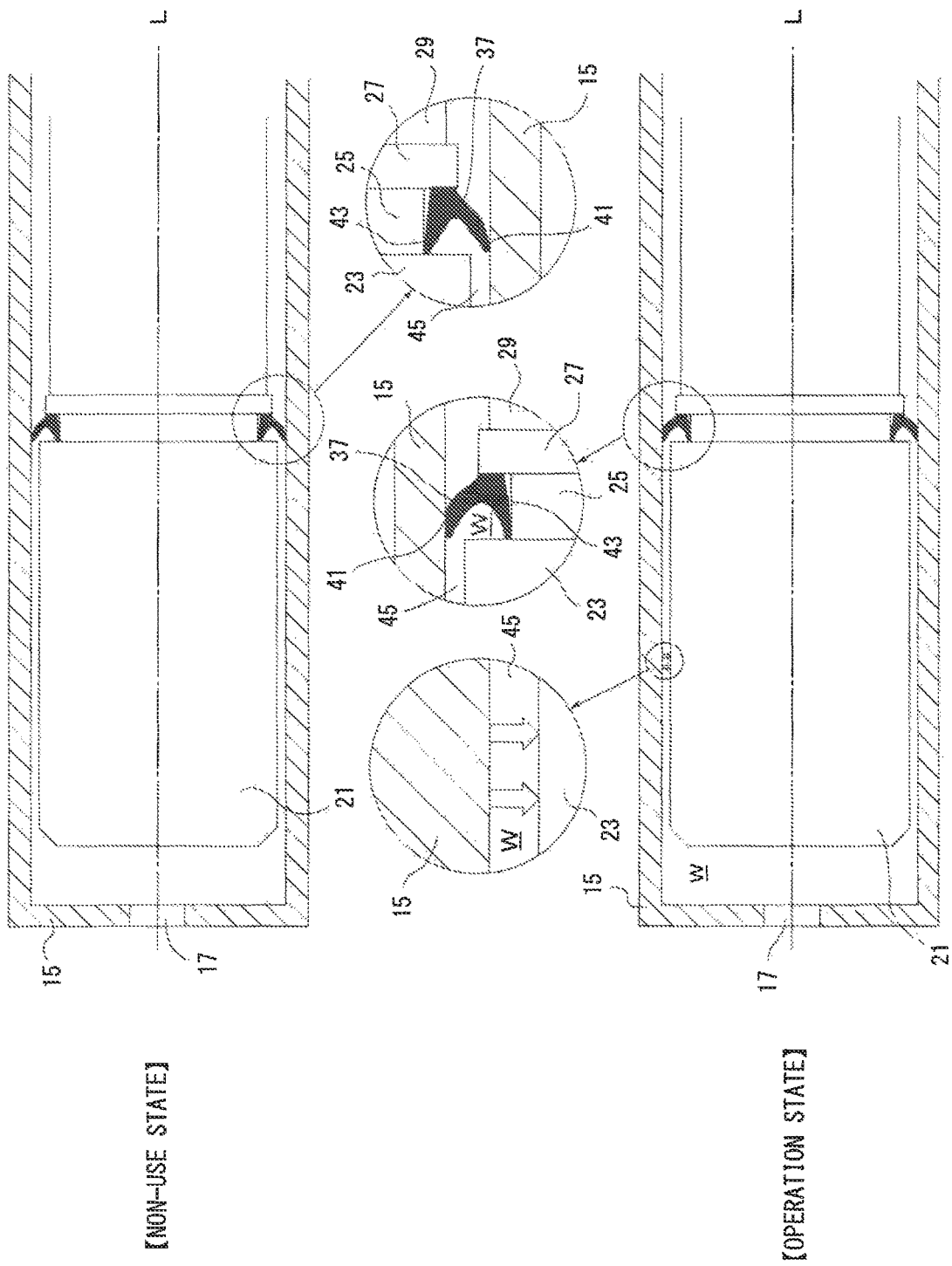
FIG. 4 is explanatory diagrams of states in which the plunger is inserted into the syringe in a non-use state and an operation state of FIG. 3.

A non-use state of FIG. 4 indicates a state in which the plunger 21 is ideally coaxially inserted into the syringe 15 and the axial length (X) of the front portion 23 of the plunger 21 is designed to 41.5 mm. Further, (Y) of the gap 45 is designed to be in the range of 0.005 to 0.045 mm.

When a liquid W (an infusion in a connection state to the infusion bag B) flows from the communication hole 17 into the syringe 15, the liquid also enters the gap 45 from the periphery of the corner portion 35 of the front end surface 33 of the plunger 21 to be filled therein and reaches the seal ring 37. Further, the plunger 21 retreats in the direction of pulling the plunger 21 in proportion to an increase in capacity of the liquid W during the inflow of the liquid. At this time, as illustrated in the operation state of FIG. 4, the liquid pressure is received by the inner bottom side of the seal ring 37 so that the tapered outer wall portion 41 and the inner wall portion 43 are respectively elastically enlarged. Thus, since the contact areas of the sealing ring on the side of the syringe 15 and the side of the relay portion 25 of the plunger 21 increase so that seal strength increases, a sealing mechanism is realized. Accordingly, a liquid leakage is prevented.

Further, since the liquid W enters the gap 45 to be filled therein, the outer peripheral surface of the front portion 23 of the plunger 21 receives a liquid pressure as indicated by an arrow. Since the front portion 23 has a length (X) to a certain degree, an area that receives the liquid pressure sufficiently increases. For that reason, the plunger 21 is in a cantilevered state firmly while being held by the liquid W. That is, it is possible to realize a centering function that aligns the center axis of the plunger 21 to the center axis (L) inside the syringe 15. Further, since the holding side is the liquid, the movement of the plunger 21 in the retreating direction is not disturbed.

In the inspection machine 1, since the backward movement of the plunger 21 in the axial direction is a measurement target and a stable centering function is realized during the movement of the plunger 21, the flow rate of the liquid W is accurately reflected to the movement amount of the plunger 21 and hence a measurement can be performed with high accuracy.

Additionally, although air originally existing in the syringe 15 remains as it is in the syringe 15, the amount is small and hence this is not illustrated in the drawings.

Figure 5:
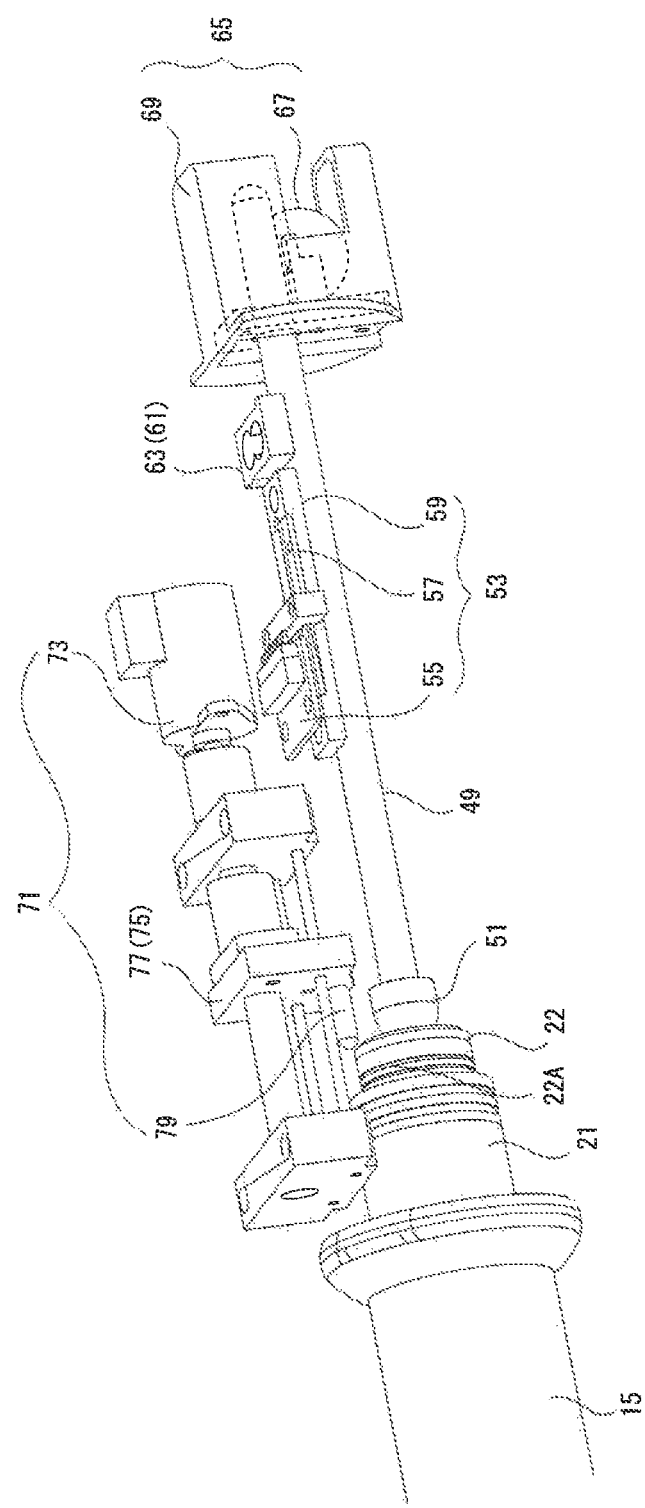
FIG. 5 is an explanatory diagram of a measurement unit of the inspection machine of FIG. 1.

The other side of the casing body 5 in the longitudinal direction (the right side in FIG. 2) serves as a measurement unit 47. In the measurement unit 47, the casing body 5 has a box shape and protrudes with respect to the syringe setting portion 7. Here, various things illustrated in FIG. 5 are accommodated therein. Further, a part of the rear portion 29 of the plunger 21 enters the casing body 5.

Reference numeral 49 denotes a measurement shaft, the measurement shaft 49 is coaxially disposed with respect to the plunger 21, and a hemispherical cap 51 on the front end side abuts against a cap 22 of the plunger 21. Thus, when the plunger 21 moves in the retreating direction, the measurement shaft 49 also retreats in the axial direction in a synchronization manner.

An optical detector 53 is disposed along the measurement shaft 49. A reflection board 55 equipped with light emitting and receiving elements as the optical detector 53 is fixed to the casing body 5 and a scale 57 provided with a plurality of slits is fixed to the measurement shaft 49 through a scale base 59.

When the scale 57 moves in synchronization with the movement of the measurement shaft 49, the amount of the light radiated from the light emitting element of the reflection board 55, reflected by the scale 57, and returned to the light receiving element changes. Accordingly, the movement amount of the plunger 21 is calculated by a change in the light amount.

Further, an occlusion pressure detector 61 is disposed at a position adjacent to the optical detector 53 along the measurement shaft 49. A distortion body 63 which is the occlusion detector 61 is fixed to the casing body 5 and a distortion gauge (not illustrated) is attached thereto.

The distortion body 63 faces the scale base 59 from the retreating direction and the scale base 59 is used as an external force applying member. Thus, when the scale base 59 retreats as the plunger 21 excessively retreats, the distortion body 63 is pushed and distorted and hence the distortion amount is used as an occlusion pressure (electric) signal.

Further, a pseudo dripper 65 is attached to the base end portion of the measurement shaft 49. The pseudo dripper 65 is provided with a light transmission filter board 67. The filter board 67 is rotatable and the transmission changes in accordance with the angle. A body portion 69 is provided so as to surround the filter board 67. The body portion 69 serves as a portion which is attached instead of the drip chamber and is formed in a shape sandwiching and fixing the drip sensor T as illustrated in FIG. 1. When the filter board 67 is attached to the inspection machine 1 in this posture, the filter board 67 faces the detection optical path of the drip sensor T.

The cap 22 is inserted into the buttocks of the plunger 21 to be blocked and a step surface 22A perpendicular to the axial direction is formed. A locking mechanism 71 which locks the backward movement of the plunger 21 using the step surface 22A is configured.

A motor 73 is fixed to the casing body 5 and a push shaft 79 connected to a nut 77 through a ball screw 75 moves forward and backward in the axial direction as the motor 73 rotates. When the push shaft 79 advances toward the plunger 21, the push shaft abuts against the step surface 22A so that the plunger 21 is pushed back into the syringe 15. When the motor 73 is stopped here, the plunger 21 is locked to a predetermined standby position inside the syringe 15. Then, when the push shaft 79 is caused to retreat, the push shaft is separated from the plunger 21 so that a locking is released.

FIG. 6 is a schematic electric configuration diagram of the inspection machine 1.

As illustrated in this drawing, the entire machine is controlled mainly by a CPU 81 of a microcomputer mounted on a main board together with a memory and the like. When power is supplied from a built-in battery 83 and the machine is activated by tuning on a power switch 85, detection signals are transmitted from the optical detector 53 and the occlusion pressure detector 61, so that the rotational driving of the filter board 67 of the pseudo dripper 65 and the motor 73 of the locking mechanism 71 is controlled and calculation results of a flow rate and an occlusion pressure are displayed on an LCD (a display unit) 87. The LCD 87 is provided on the upper surface of the casing body 5.

A radio communication unit (Bluetooth (trademark)) 89 and a USB connector 91 are further connected to the CPU 81 and the recording, changing, and the like of data of the memory can be performed by an external computer. That is, it is possible to change data necessary for calculating the occlusion pressure or the flow rate such as the inner diameter of the syringe 15.

Further, an alarm buzzer 93 is also connected thereto. Accordingly, when an abnormally high occlusion pressure is detected, this abnormality is notified promptly and hence the failure of the infusion pump P can be prevented.

Since the inspection machine 1 has the above-described configuration, when the machine is set as illustrated in FIG. 1 and is activated, a pseudo signal is received by the infusion pump P so that the pump operation starts and the liquid W is fed into the syringe 15. Accordingly, the plunger 21 moves backward along with the measurement shaft 49 and the flow rate or the occlusion pressure illustrating the operation state of the infusion pump P is successively displayed on the LCD 87 by the detection of the occlusion pressure detector 61 or the optical detector 53 in that state. Thus, it is possible to check and inspect the operation state of the infusion pump P from this display result. As described above, since the movement amount of the plunger 21 is accurately reflected to the flow rate of the liquid W, the data of the flow rate or the occlusion pressure is highly reliable.

Further, since the liquid W used for measurement is not dripped but is stored in the syringe 15, preparation of a drainage is not necessary.

After the checking and inspecting operation ends, the motor 73 is driven so that the plunger 21 is pushed back by the push shaft 79, is returned to an initial position, and is locked at that position. Additionally, strictly speaking, the movement of the plunger 21 in the advancing direction is free.

Figure 7:
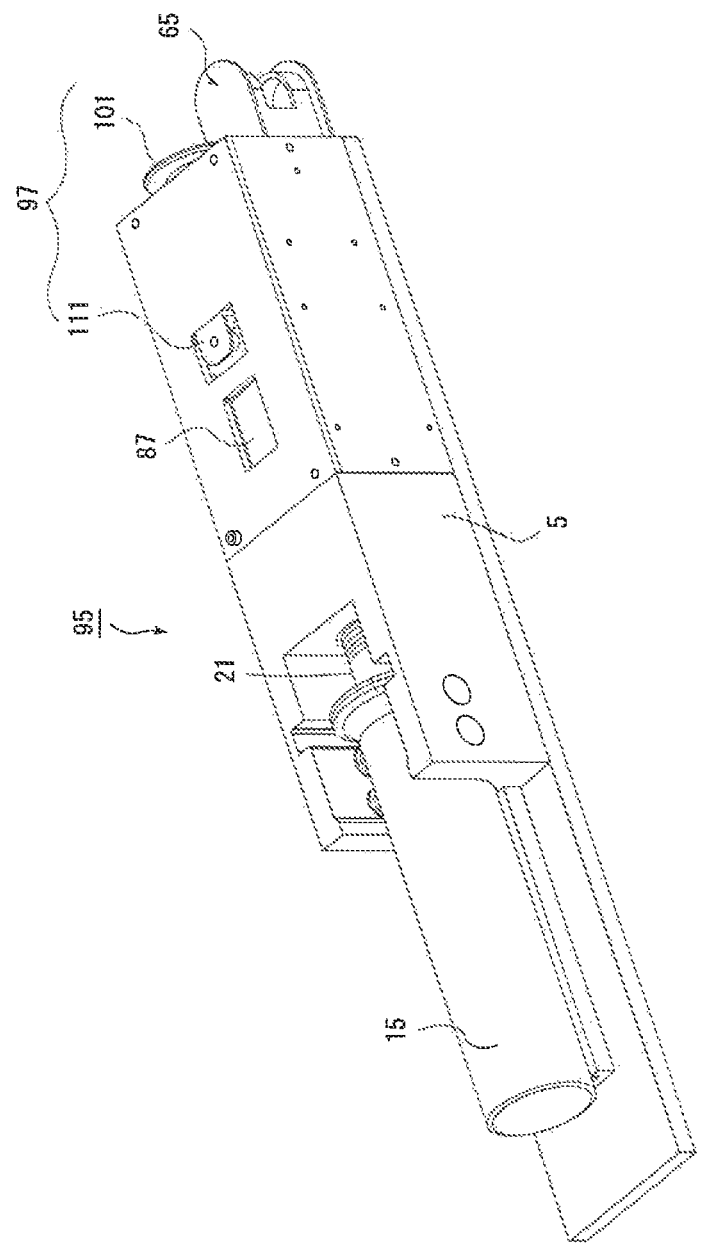
FIG. 7 is a perspective view of an infusion pump inspection machine according to a second embodiment of the invention.

FIG. 7 illustrates an inspection machine 95 according to a second embodiment of the invention.

The inspection machine 95 has substantially the same configuration as that of the inspection machine 1 according to the first embodiment. Since that part is denoted by the same reference numerals, a description thereof will be omitted and only an obviously different part will be described.

The inspection machine 95 is a simple type and hence the casing accommodating the infusion bag B is not provided in advance.

Figure 8:
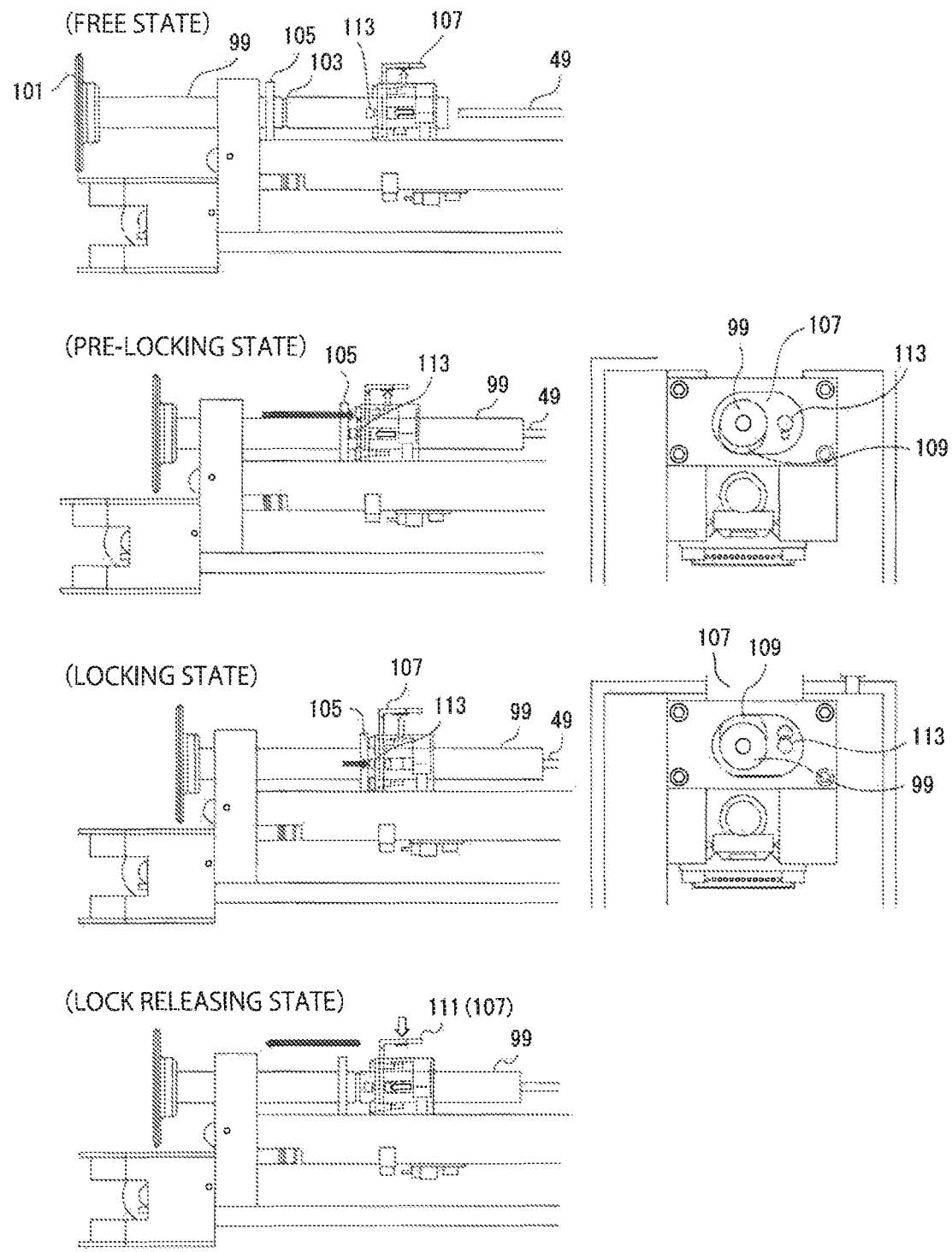
FIG. 8 is an explanatory diagram of a locking mechanism of FIG. 7.

Further, a locking mechanism 97 has a mechanical configuration and can be manually locked and released. That is, a plate-shaped locking operation portion 101 is connected to abase end of a push shaft 99 and the locking operation portion 101 protrudes outward from the casing body 5. As illustrated in FIG. 8, the front end of the push shaft 99 is disposed so as to coaxially abut against the measurement shaft 49. The outer peripheral surface of the push shaft 99 is provided with an annular locking groove 103 and a flange-shaped abutting surface 105.

The push shaft 99 passes through a locking hole 109 of a locking piece 107. The locking piece 107 is bent in an "L-shape", a perpendicular portion is provided with the locking hole 109, and a horizontal portion protrudes upward as a release operation portion 111 from an upper surface opening of the casing body 5.

The locking piece 107 is elastically urged upward as indicated by an arrow by a spring. However, in a free state, the locking piece 107 is lowered and held at a low height position due to a press contact force of a free holding pin 113 in the horizontal direction indicated by an arrow. Then, when the push shaft 99 pushes the measurement shaft 49 as indicated by a black arrow, the push shaft 99 smoothly passes through the locking hole 109. When the push shaft 99 moves to a position near a locking position, the abutting surface 105 of the push shaft 99 abuts against the free holding pin 113 as indicated by an arrow. When the push shaft 99 is further moved, the free holding pin 113 is pushed as indicated by an arrow so that a press contact state is released and the locking piece 107 is only applied with an urging force indicated by an arrow so that the locking groove 103 is fitted in and locked to the locking hole 109 to become a locking state. In this locking state, when the release operation portion 111 is pushed down as indicated by an arrow, the locking piece 107 is lowered so that the locking groove 103 is separated from the locking hole 109. Accordingly, when the push shaft 99 is caused to retreat as indicated by a black arrow, the abutting surface 105 also retreats and the press contact force of the free holding pin 113 is acted again so as to return to the free state.

As described above, although the embodiment of the invention has been described in detail, a specific configuration is not limited to this embodiment. Then, a modification in design and the like without departing from the scope of the invention are also included in the invention.

For example, in the above-described embodiment, the infusion pump of the drip rate control type is an inspection target, but the infusion pump of the flow rate control type can also be an inspection target.

REFERENCE SIGNS LIST

1 Inspection machine (first embodiment)
3 Casing
5 Casing body
7 Syringe setting portion
9 Bed recess
11 Guard pipe
13 Locking recess
15 Syringe
17 Communication hole
19 Tube connection portion
21 Plunger
22 Cap
22A Step surface
23 Front portion
25, 27 Relay portion
29 Rear portion
31 Annular recess
33 Front end surface
35 Corner portion
37 Seal ring
39 Outer bottom surface
41 Outer wall portion
43 Inner wall portion
45 Gap
47 Measurement unit
49 Measurement shaft
51 Cap
53 Optical detector
55 Reflection board
57 Scale
59 Scale base
61 Occlusion pressure detector
63 Distortion body
65 Pseudo dripper
67 Filter board
69 Body portion
71 Locking mechanism
73 Motor
75 Ball screw
77 Nut
79 Push shaft
81 CPU
83 Battery
85 Power switch
87 LCD (display unit)
89 Radio communication unit
91 USB connector
93 Alarm buzzer
P Infusion pump
C Tube
B Infusion bag
T Drip sensor
95 Inspection machine (second embodiment)
97 Locking mechanism
99 Push shaft
101 Locking operation portion
103 Locking groove
105 Abutting surface
107 Locking piece
109 Locking hole
111 Release operation portion
113 Free holding pin

The invention claimed is:

1. An infusion pump inspection machine comprising:
   a syringe which has a tube connection communication hole provided in a front end side in an axial direction; and
   a plunger which is inserted into the syringe by forming a gap so that the plunger is movable forward and backward in the axial direction,
   wherein an operation of an infusion pump is checked and inspected by a liquid flowing into the syringe through the communication hole with the driving of the infusion pump and moving the plunger backward,
   wherein an outer peripheral surface of the plunger is provided with an annular recess,
   wherein a seal ring is fitted to the annular recess, and
   wherein a sealing mechanism is created by a liquid pressure of a liquid flowing into the syringe and filling into the gap so as to expand the seal ring and to increase a contact area with an inner peripheral surface of the syringe and a centering mechanism which coaxially centers the plunger to the syringe.

2. The infusion pump inspection machine according to claim 1,
   wherein the seal ring is a V-shaped seal ring which is fitted so that a V-shaped sharp inner bottom portion faces a base end side of the plunger in the axial direction, and
   wherein the sealing mechanism receives a liquid pressure to expand the V-shape of the seal ring and to increase a contact area with the inner peripheral surface of the syringe.

3. The infusion pump inspection machine according to claim 1,
   wherein the plunger is formed to have the same diameter on the front end side in relation to a fitting surface of the seal ring.

4. The infusion pump inspection machine according to claim 1,
   wherein a locking mechanism for locking a relative movement of the plunger with respect to the syringe and releasing the locking is provided.

5. The infusion pump inspection machine according to claim 1,
   wherein as the measurement unit, a measurement shaft which is provided coaxially with the plunger and moves in synchronization with a backward movement of the plunger, an optical detector which detects a light amount which changes by the movement of the measurement shaft, and a distortion detector which detects distortion generated by the pressing of the measurement shaft are provided, and
   wherein a delivery flow rate is calculated on the basis of a detection result of the optical detector and an occlusion pressure is calculated on the basis of a detection result of the distortion detector.

6. The infusion pump inspection machine according to claim 1,
   wherein as a pseudo drip signal generator, a pseudo dripper which generates a pseudo drop and an attachment guide portion which attaches a drip sensor of the infusion pump to a position for detecting the pseudo drop are provided.

7. The infusion pump inspection machine according to claim 1, further comprising:
   an accommodation portion for a soft bag filled with an infusion.

* * * * *